United States Patent [19]

Diana

[11] 4,009,170

[45] Feb. 22, 1977

[54] 1-ETHOXY-3,4-DIHYDROISOQUINDINES

[75] Inventor: Guy D. Diana, Stephentown, N.Y.

[73] Assignee: Sterling Drug Inc., New York, N.Y.

[22] Filed: Aug. 1, 1972

[21] Appl. No.: 277,051

Related U.S. Application Data

[63] Continuation-in-part of Ser. No. 62,700, Aug. 10, 1970, Pat. No. 3,753,994.

[30] Foreign Application Priority Data

Aug. 6, 1971 Canada .............................. 120032

[52] U.S. Cl. .......................................... 260/289 R
[51] Int. Cl.$^2$ .................................... C07D 217/24
[58] Field of Search ............................... 260/289 R

[56] References Cited

UNITED STATES PATENTS

| | | | |
|---|---|---|---|
| 3,301,857 | 1/1967 | Berger et al. | 260/288 |
| 3,437,662 | 4/1969 | Gildersleve et al. | 260/286 |
| 3,560,620 | 2/1971 | Schor et al. | 424/258 |
| 3,597,431 | 8/1971 | Coppola et al. | 260/288 |

OTHER PUBLICATIONS

Chem. Abstracts 61:7575e (1964).

*Primary Examiner*—G. Thomas Todd
*Attorney, Agent, or Firm*—Theodore C. Miller; B. Woodrow Wyatt

[57] ABSTRACT

1-(2-Substituted-hydrazino)-3,4-dihydroisoquinolines, prepared in one process by alkylating the corresponding 3,4-dihydroisocarbostyrils, hydrazinolyzing the resulting 1-alkoxy-3,4-dihydroisoquinolines and condensing the resulting 1-hydrazIno-3,4-dihydroisoquinolines with aldehydes or ketones, and 1,1'-azinobis(1,2,3,4-tetrahydroisoquinolines), prepared by condensing corresponding 1-alkoxy-3,4-dihydroisoquinolines and 1-hydrazino-3,4-dihydroisoquinolines, are useful as antihypertensive agents and/or as antiinflammatory agents.

5 Claims, No Drawings

1-ETHOXY-3,4-DIHYDROISOQUINDINES

This application is a continuation-in-part of my prior copending application Ser. No. 62,700, filed Aug. 10, 1970, now U.S. Pat. No. 3,753,994.

This invention relates to new and useful compositions of matter classified in the art of chemistry as isoquinolines and to processes for their preparation.

In one of its composition of matter aspects my invention provides 1-[2-(X,X'-methylene)hydrazino]-3-(Y)-4-(Y')-6-(Z)-7-(Z')-3,4-dihydroisoquinoline of the formula

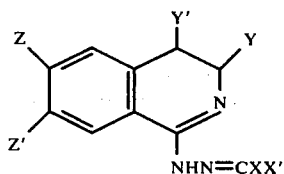

(Formula I), wherein

X, when taken alone, is hydrogen; alkyl of one to six carbon atoms; alkenyl of two to six carbon atoms; cycloalkyl of three to seven ring atoms and three to ten carbon atoms; cycloalkenyl of five to seven ring atoms and five to ten carbon atoms; phenyl or phenyl substituted by one to three members of the group consisting of halo, hydroxy, atertiary alkyl of one to four carbon atoms and atertiary alkoxy of one to four carbon atoms; styryl substituted in the benzene ring by a member of the group consisting of halo, hydroxy, atertiary alkyl of one to four carbon atoms, atertiary alkoxy of one to four carbon atoms of di-(atertiary alkyl of one to four carbon atoms)-amino; or, when Y is hydrogen, α-(atertiary alkyl of one to four carbon atoms)-styryl or α-(atertiary alkyl of one to four carbon atoms)-styryl substituted in the benzene ring by a member of the group consisting of halo or atertiary alkyl of one to four carbon atoms;

X', when taken alone, is hydrogen of atertiary alkyl of one to four carbon atoms;

X and X', when taken together with C, are cycloalkylidene of five to seven ring atoms and five to ten carbon atoms;

Y'' is hydrogen or atertiary alkyl of one to four carbon atoms;

Y' is hydrogen, atertiary alkyl of one to four carbon atoms, phenyl, hydroxy or atertiary alkoxy of one to four carbon atoms;

Z and Z', when taken alone, are the same or different and are hydrogen, atertiary alkyl of one to four carbon atoms, halo, hydroxy or atertiary alkoxy of one to four carbon atoms;

Z and Z', when taken together, are methylenedioxy and acid addition salts thereof.

In another of its composition of matter aspects my invention provides 1,1'-azinobis[3-(Y)-4-(Y')-6-(Z)-7-(Z!)-1,2,3,4-tetrahydroisoquinoline] of the formula

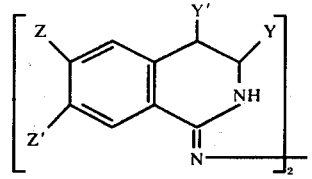

(Formula II), wherein Y, Y', Z and Z' have the same meanings ascribed thereto above in Formula I, and acid addition salts thereof.

The isoquinolines of Formulas I and II and acid addition salts thereof have antihypertensive activity and/or antiinflammatory activity and are useful as antihypertensive agents and/or as antiinflammatory agents.

In still another of its composition of matter aspects my invention provides 1-(QO)-3-(Y)-4-(Y')-6-(Z)-7-(Z')-3,4-dihydroisoquinoline of the formula

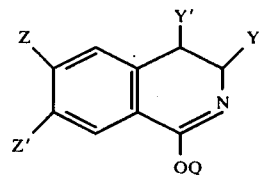

(Formula III), wherein Q is methyl, ethyl or propyl and Y, Y', Z and Z' have the meanings ascribed thereto above in Formula I, and acid addition salts thereof.

The isoquinolines of Formula III and acid addition salts thereof are useful as intermediates in preparing the isoquinolines of Formulas I and II.

In one of its process aspects my invention provides the process for producing 1-[2-(X,X 40 -methylene)-hydrazino]-3-(Y)-4-(Y')-6-(Z)-7-(Z')-3,4-dihydroisoquinoline of Formula I which comprises the steps of alkylating 3-(Y)-4-(Y')-6-(Z)-7-(Z')-3,4-dihydroisocarbostyril of the formula

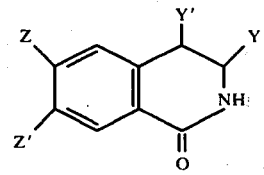

(Formula IV), with a $Q_3O^+$ salt, wherein Q is methyl, ethyl or propyl, hydrazinolyzing the resulting 1-(QO)-3-(Y)-4-(Y')-6-(Z)-7-(Z')-3,4-dihydroisoquinoline of Formula III or an acid addition salt thereof, and condensing the resulting 3-(Y)-4-(Y')-6-(Z)-7-(Z')-1-hydrazino-3,4-dihydroisoquinoline of the formula

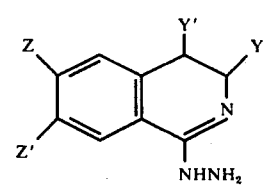

(Formula V)

or an acid addition salt thereof with an aldehyde or a ketone of the formula O-CXX'.

In another of its process aspects my invention provides the process for producing 1-[2-(X,X'-methylene)hydrazino]-3-(Y)-4-(Y')-6-(Z)-7-(Z')-3,4-dihydroisoquinoline of Formula I which comprises the steps of alkylating 3-(Y)-4-(Y')-6-(Z)-7-(Z')-3,4-dihydroisocarbostyril of Formula IV with a $Q_3O^+$ salt, wherein Q is methyl, ethyl or propyl, ammonolyzing the resulting 1-(QO)-3-(Y)-4-(Y')-6-(Z)-7-(Z')-3,4-dihydroisoquinoline of Formula III with an $RR'NH_2^+$ salt, wherein R and R', when taken alone, are the same or different and are hydrogen, atertiary alkyl of one to four carbon atoms, cycloalkyl of five to seven ring atoms and five to ten carbon atoms, or phenylalkyl of seven to ten carbon atoms, and wherein R and R', when taken together with N, are 1-pyrrolidinyl, piperidino or morpholino, hydrazinolyzing the resulting 1-(RR'N)-3-(Y)-4-(Y')-6-(Z)-7-(Z')-3,4-dihydroisoquinoline of the formula

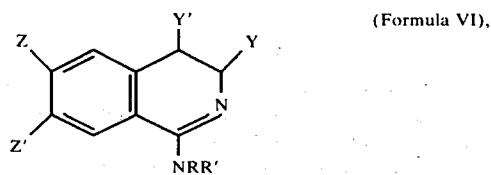

(Formula VI), and condensing the resulting 3-(Y)-4-(Y')-6-(Z)-7-(Z')-1-hydrazino-3,4-dihydroisoquinoline of Formula V or an acid addition salt thereof with an aldehyde or a ketone of the formula O-CXX'.

In still another of its process aspects my invention provides the process for producing 1-[2-(X,X'-methylene)hydrazino]-3-(Y)-4-(Y')-6-(Z)-7-(Z')-3,4-dihydroisoquinoline of Formula I which comprises the steps of cyclizing 1-{1-(Y)-2-(Y')-2-[3-(Z)-4-(Z')-phenyl]ethyl}-3-($T_n$-phenyl)urea, wherein T is hydrogen, halo or atertiary alkoxy of one to four carbon atoms and n is one to three, of the formula

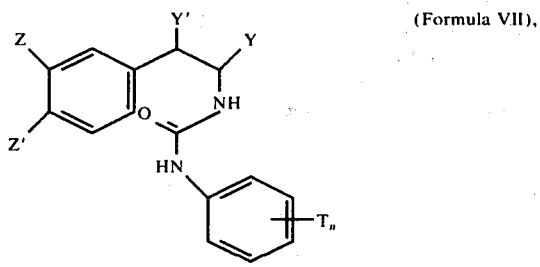

(Formula VII), hydrazinolyzing the resulting 1-($T_n$-anilino)-3-(Y)-4-(Y')-6-(Z)-7-(Z')-3,4-dihydroisoquinoline of the formula

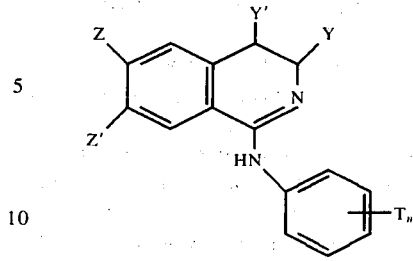

(Formula VIII), and condensing the resulting 3-(Y)-4-(Y')-6-(Z)-7-(Z')-1-hydrazino-3,4-dihydroisoquinoline of Formula V or an acid addition salt thereof with an aldehyde or a ketone of the formula O-CXX'.

In yet another of its process aspects my invention provides the process for producing 1,1'-azinobis[3-(Y)-4-(Y')-6-(Z)-7-(Z')-1,2,3,4-tetrahydroisoquinoline] of Formula II which comprises the step of condensing 1-(QO)-3-(Y)-4-(Y')-6-(Z)-7-(Z')-3,4-dihydroisoquinoline of Formula III with the corresponding 3-(Y)-4-(Y')-6-(Z)-7-(Z')-1-hydrazino-3,4-dihydroisoquinoline of Formula V.

When X of Formula I is alkyl of one to six carbon atoms, alkyl can be branched or unbranched alkyl, as illustrated by methyl, ethyl, propyl, isopropyl, butyl, isobutyl, sec-butyl, tert-butyl, pentyl and hexyl.

When X of Formula I is alkenyl of two to six carbon atoms, alkenyl can be branched or unbranched alkenyl as illustrated by vinyl, allyl, 1-methyl-1-propenyl and 2-hexenyl.

When X of Formula I is cycloalkyl of three to seven ring carbon atoms, cycloalkyl can be branched or unbranched cycloalkyl as illustrated by cyclopropyl, cyclopentyl, cyclohexyl, 4-methylcyclohexyl or cycloheptyl. When R and/or R' of Formula VI is cycloalkyl of five to seven ring carbon atoms, cycloalkyl can be branched or unbranched cycloalkyl.

When X of Formula I is cycloalkenyl of five to seven ring carbon atoms, cycloalkenyl can be branched or unbranched cycloalkenyl as illustrated by 1-cyclopentenyl, 3-cyclohexenyl, 4-methyl-3-cyclohexenyl or 1-cycloheptenyl.

Halo as used herein means fluoro, chloro, bromo or iodo.

Atertiary as used herein means not tertiary. Thus, atertiary alkyl of one to four carbon atoms is methyl, ethyl, propyl, isopropyl, butyl, isobutyl or sec-butyl and atertiary alkoxy of one to four carbon atoms is methoxy, ethoxy, propoxy, isopropoxy, butoxy, isobutoxy or sec-butoxy.

When X of Formula I is substituted phenyl, it is, for example, p-bromophenyl, m-hydroxyphenyl, p-tolyl, 2,3-dimethoxyphenyl or 3,5-dimethoxy-4-hydroxyphenyl.

When X of Formula I is substituted styryl, it is, for example, m-bromostyryl, p-hydroxystyryl, p-methylstyryl, p-methoxystyryl or p-dimethylaminostyryl.

When X of Formula I is substituted α-(atertiary alkyl of one to four carbon atoms)-styryl, it is, for example, α-methyl-p-florostyryl, α-methyl-p-chlorostyryl, α-methyl-o-chlorostyryl or α,p-dimethylstyryl.

When X and X', taken together with C, are cycloalkylidene of five to seven ring carbon atoms, cycloalkylidene can be branched or unbranched cycloalkylidene as illustrated by cyclopentylidene, cyclohexylidene, 4-methylcycloalkylidene or cycloheptylidene.

The manner and process of making and using the invention and the best mode of carrying it out will now be described so as to enable any person skilled in the art to which it pertains to make and use it.

Alkylation of 3-(Y)-4-(Y')-6-(Z)-7-(Z')-3,4-dihydroisocarbostyril of Formula IV is accomplished using a $Q_3O^+$ (trialkyloxonium) salt in a dry solvent inert under the reaction conditions at a temperature in the range of $-10°$ C. to $110°$ C. The preferred trialkyloxonium salt is triethyloxonium fluoborate. Methylene dichloride is the preferred solvent, although other solvents, for example, benzene, chloroform, dioxane, tetrahydrofuran, N,N-dimethylformamide or mixtures thereof can also be used.

Hydrazinolysis of 1-(QO)-, 1-(RR'N)- and 1-($T_n$-anilino)-3-(Y)-4-(Y')-6-(Z)-7-(Z')-3,4-dihydroisoquinoline of Formulas III, VI and VIII, respectively, or an acid addition salt of the first, for example, the fluoborate, is carried out using hydrazine or an acid addition salt thereof in a solvent inert under the reaction conditions at a temperature in the range of 0°–100° C. Ethanol is the preferred solvent, although other solvents, for example, methanol, 2-propanol, acetonitril, dimethylsulfoxide, N,N-dimethylformamide or mixtures thereof can also be used. Hydrazionolyzing 1-(QO)-3-(Y)-4-(Y')-6-(Z)-7-(Z')-3,4-dihydroisoquinoline of Formula III with hydrazine also produces 1,1'-azinobis[3-(Y)-4-(Y')-6-(Z)-7-(Z')-1,2,3,4-tetrahydroisoquinoline] of Formula II, formation of which is diminished by using an acid addition salt of hydrazine, for example, hydrazine monohydrochloride.

Condensation of 3-(Y)-4-(Y')-6-(Z)-7-(Z')-1-hydrazino-3,4-dihydroisoquinoline of Formula V or an acid addition salt thereof, for example, the hydrochloride, with an aldehyde or a ketone of the formula O-CXX' is achieved with or without a diluent at a temperature in the range of 0°–120° C. If a diluent is used, it can be any solvent inert under the reaction conditions, for example, methanol, ethanol, ether, benzene, tetrahydrofuran or mixtures thereof.

Ammonolysis of 1-(QO)-3-(Y)-4-(Y')-6-(Z)-7-(Z')-3,4-dihydroisoquinoline of Formula III is performed using an $RR'NH_2^+$ (ammonium) salt in a solvent inert under the reaction conditions at a temperature in the range of 0°–120° C. The preferred ammonium salt is ammonium chloride and the preferred solvent is methanol. Other solvents which can be used are, for example, ethanol, 1-propanol, 2-propanol, acetonitrile, dimethylsulfoxide, N,N-dimethylformamide or mixtures thereof.

Cyclization of 1-{1-(Y)-2-(Y')-[3-(Z)-4-(Z')-phenyl]-ethyl}-3-($T_n$-phenyl)urea of Formula VII is done using a mixture of phosphorus oxychloride and phosphorus pentoxide with or without a diluent at a temperature in the range of 50°–150° C. The preferred conditions are an approximately 3:1 phosphorus oxychloride-phosphorus pentoxide mixture without a diluent at the reflux temperature of the mixture. If a diluent is used, it can be any solvent inert under the reaction conditions, for example, benzene or chlorobenzene.

Condensation of 1-(QO)-3-(Y)-4-(Y')-6-(Z)-7-(Z')-3,4-dihydroisoquinoline of Formula III with 3-(Y)-4-(Y')-6-(Z)-7-(Z')-1-hydrazino-3,4-dihydroisoquinoline of Formula V or an acid addition salt thereof is effected using a solvent inert under the reaction conditions at a temperature in the range of 0°–100° C. Methanol is the preferred solvent, although other solvents, for example, ethanol, 1-propanol, 2-propanol, acetonitrile, dimethylsulfoxide, N,N-dimethylformamide or mixtures thereof can also be used.

Acid addition salts of the isoquinolines of Formulas I and II of my invention can be prepared with any pharmaceutically acceptable inorganic (mineral) or organic acid. If inorganic, the acid can be, for example, hydrochloric acid, hydrobromic acid, nitric acid, phosphoric acid, sulfuric acid or sulfamic acid. If organic, the acid can be, for example, acetic acid, glycolic acid, lactic acid, quinic acid, hydrocinnamic acid, succinic acid, tartaric acid, citric acid, methanesulfonic acid or benzenesulfonic acid.

For the pharmaceutical purposes of this invention the free base forms of the isoquinolines of Formulas I and II and their corresponding acid addition salts are considered to be equivalent. That the protonic acid be pharmaceutically acceptable means that the beneficial properties inherent in the free base not be vitiated by side effects ascribable to the anions.

Although pharmaceutically acceptable salts are preferred, all acid addition salts are within the scope of the invention. A pharmaceutically unacceptable salt may be useful, for example, for purposes of identification or purification or in preparing a pharmaceutically acceptable salt by ion exchange procedures.

When crystalline, the isoquinolines of Formulas I–VIII and their acid addition salts are purified by recrystallization and are characterized by their melting points (m.p.). When liquid, the isoquinolines of Formulas I–VIII are purified by distillation under reduced pressure and are characterized by their boiling points (b.p./mm. Hg). The structures of the isoquinolines of Formulas I–III follow from the route of synthesis and are corroborated by infrared spectral analysis, by nuclear magnetic resonance spectral analysis and by the correspondence of calculated and found values of elemental analysis of representative samples.

As stated above the isoquinolines of Formulas I and II have antihypertensive activity and/or antiinflammatory activity, each of which was tested by two methods.

In the first method for testing antihypertensive activity the renal hypertensive rat is used. The compound to be tested is administered, preferably in the form of a pharmaceutically acceptable acid addition salt, orally as a gum tragacanth suspension or subcutaneously as an aqueous solution to three hypertensive rats at each of four different dose levels graduated at 0.3 to 0.9 logarithmic intervals. The systolic blood pressure is determined for each of the three rats at each dose level before medication and at intervals of 1, 2, 4, 5, 24 and 48 hours after medication. The unmedicated rats are considered hypertensive if the systolic blood pressure is 160 millimeters of mercury or greater. The medicated rats are considered normotensive if the systolic blood pressure is 130 millimeters of mercury or less. Each blood pressure reading is judged by these criteria. The dose level of test compound which reduces the systolic blood pressure to a normotensive level in 50% of the animals is defined as the $AED_{50}$ (approximate effective dose) value. When tested in this way, isoquinolines of Formulas I and II were found to have $AED_{50}$ values in the range of 5–50 milligrams per kilogram.

In the second method for testing antihypertensive activity the renal hypertensive rat or the spontaneous hypertensive [Okamoto and Ooki, Japan Circulation J., 27, 282 (1963)] rat is used. The compound to be tested is administered, preferably in the form of a pharmaceutically acceptable acid addition salt, orally as a gum tragacanth suspension or subcutaneously as in aqueous solution at one or more dose levels to five hypertensive rats at each dose level. The systolic blood pressure of each rat is determined before medication and at 2, 6 and 24 hours after medication. Of the values of the systolic blood pressure of each rat determined at 2, 6 and 24 hours which are lower than the premedication value, the lowest value is chosen. The difference between the premedication value and the lowest value is the maximum lowering of the systolic blood pressure and the maximum lowerings are averaged for each group of rats. When the data permit, at least three such average maximum lowerings are plotted to determine the $AHD_{40}$ (Antihypertensive dose) value, that is, the dose which would effect an average maximum lowering of 40 millimeters of mercury. When tested in this way, isoquinolines of Formula I were found to have $AHD_{40}$ values in the range of 5–50 milligrams per kilogram.

The first method for testing antiinflammatory activity is the carrageenin edema method and is essentially that of VanArman, Begany, Miller and Pless, Journal of Pharmacology and Experimental Therapeutics 150, 328 (1965) as modified by Winter, Risley and Nuss, Proceedings of the Society for Experimental Biology and Medicine 111, 544 (1962). Young male rats weighing 100–110 grams are used. Food is withdrawn approximately 18 hours prior to medication, but the animals are permitted free access to drinking water up to the time of medication. Compounds to be tested are suspended by triturating in 1% gum tragacanth and administered by gavage in a volume of 1 milliliter per 100 grams of body weight. Control animals receive the gum tragacanth only. One hour after medication, 0.05 milliliter of a 1% suspension of carrageenin in 0.9% saline is injected into the plantar tissue of the left hind paw. Three hours after injection of the carrageenin, edema formation, that is, increase in foot volume (difference between left hind paw and the uninjected right hind paw) is measured plethysmographically in the unaesthetized rat. The extended paw is immersed to the top of the most proximal callus pad into a mercury-filled glass cylinder connected to a pressure transducer and the impulse amplified and recorded by a polygraph. The polygraph is standardized for each assay so that a deflection of 3.6 millimeters on the recording paper is equivalent to a volume of 0.1 milliliter. The results are expressed as percent inhibition calculated from the average differences in foot volume between the control and medicated rats. A compound is judged to be active if the differences in edema formation between medicated and control rats are statistically significant at the 5% level of probability. Isoquinolines of Formula I were found to be active in this test at doses in the range of 50–300 milligrams per kilogram.

The second method for testing antiinflammatory activity is the adjuvant induced arthritis method and is a modification of the methods of Pearson, Journal of Chronic Diseases 16, 863 (1963) and Glenn and Gray, American Journal of Veterinary Research 26, 1180 (1965). Adult male rats weighing 200–230 grams are used. Adjuvant (M. butyricum, 0.1 milliliter of a 0.6% suspension in heavy mineral oil) is injected into the plantar tissue of the left hind paw. A negative control group is injected with mineral oil only. Beginning on the ninth day after adjuvant injection (polyarthritis does not appear until approximately the tenth day after adjuvant administration), the animals receive 6 daily medications of test compound suspended in 1% gum tragacanth and administered by gavage in a volume of 1 milliliter per 100 grams of body weight. Both the negative control and adjuvant injected control animals receive the vehicle only. Food and water are permitted ad libitum. Twenty-four hours after the last medication, the animals are weighed, the degree of arthritic involvement, that is, increase in foot volume (difference between adjuvant injected left hind paw and uninjected right hind paw) and plasma inflammation units are determined. Foot volume is measured plethysmographically in the unanesthetized rat. The extended paw is immersed to the top of the most proximal callus pad into a mercury-filled glass cylinder connected to a pressure transducer and the impulse amplified and recorded by a polygraph. The polygraph is standardized for each assay so that a deflection of 3.6 millimeters on the recording paper is equivalent to a volume of 0.1 milliliter. The results are expressed as percent inhibition calculated from the average differences in foot volume between the adjuvant injected control and medicated rats correcting for difference in foot volume of the oil injected negative control group. Following foot volume measurements, the animals are etherized and bled by heart puncture into rubber stoppered evacuated glass tuber (calibrated to draw 2.7 milliliters) containing 0.3 milliliter of 0.1 M sodium oxalate solution for determination of plasma inflammation units. The unclotted blood is centrifuged and 0.1 milliliter of the plasma is diluted with 5.0 milliliter 5.0 milliliter of 0.9% sodium chloride solution. The plasma inflammation units are direct spectrophotometer optical density readings expressed as the difference between preheated and heated (30 minutes at 56° C.) plasma, corrected for 1:50 dilution. The results are expressed as percent inhibition calculated from the difference between the average plasma inflammation units of oil injected negative control rats. A compound is judged to be active if the differences between medicated and adjuvant injected controls are statistically significant at the 5% level of probability. Isoquinolines of Formula I were found to be active in this test at doses in the range of 50–300 milligrams per kilogram.

The preparation of the intermediates of Formulas IV and VII will now be described. In Formulas IV–VIII above and in Formulas IX–XIII which follow, Y, Y', Z and Z' have the meanings ascribed thereto above in Fromula I.

Those 3-(Y)-4-(Y')-6-(Z)-7-(Z')-3,4-dihydroisocarbostyrils of Formula IV which are not described in the chemical literature can be prepared, for example, by polyphosphoric acid cyclization of the corresponding methyl or ethyl N-{1-(Y)-2-(Y')-2-[3-(Z)-4-(Z')-phenyl]ethyl} carbamates of the formula

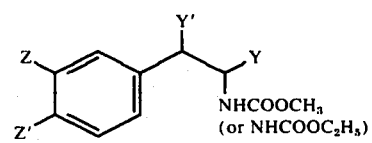

(Formula IX)

which, in turn, can be prepared from methyl or ethyl chloroformate and the corresponding 1-(Y)-2-(Y')-2-[3-(Z)-4-(Z')-phenyl]-ethylamines of the formula

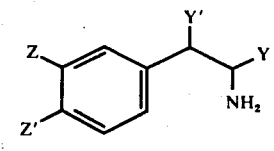
(Formula X).

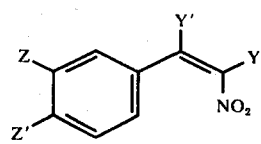
(Formula XII).

Those 3-(Y)-4-(Y')-6-(Z)-7-(Z')-3,4-dihydroisocarbostyrils of Formula IV wherein Y' is hydroxyl and which are not described in the chemical literature can also be prepared by rearrangement of the corresponding 1-[(Y)-aminometyl]-5-(Z')-6-(Z)-phthalides of the formula

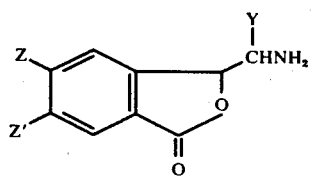
(Formula Xa)

by means of, for example, sodium hydroxide. The 1-[(Y)-aminomethyl]-5-(Z')-6-(Z)-phthalides of Formula Xa can be prepared, for example, by reduction of the corresponding 1-[(Y)-nitromethyl]-5-(Z')-6-(Z)-phthalides of the formula

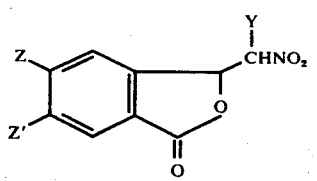
(Formula Xb)

by means of, for example, hydrogen over palladium-on-carbon. The 1[(Y)-nitromethyl]-5-(Z')-6-(Z)-phthalides of formula Xb can be prepared, for example, by condensation of 4-(Z)-5-(Z')-2-formylbenzoic acid of the formula

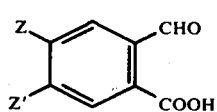
(Formula Xc)

with (Y)-nitromethane by means of, for example, sodium hydroxide.

Some of the 1-(Y)-2(Y')-2-[3-(Z)-4-(Z')-phenyl]-ethylamines of Formula X are commercially available. Those which are not commercially available and are not described in the chemical literature can be prepared, for example, by catalytic hydrogenation of the corresponding 1-(Y)-2-(Y')-2-[3(Z)-4-(Z')-phenyl]-1-nitroethanes of the formula

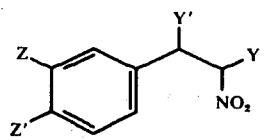
(Formula XI).

or the corresponding 1-(Y)-2-(Y')-2-[3-(Z)-4-(Z')-phenyl]-1-nitroethylenes of the formula Formula XI particularly refers to those 1-(Y)-2(Y')-2-[3-(Z)-4-(Z')-phenyl]-1-nitroethanes wherein Y' is atertiary alkoxy of one to four carbon atoms, which can be prepared from the 1-(Y)-2(Y')-2-[3-(Z)-4-(Z')-phenyl]-1-nitroethylenes of Formula XII wherein Y' is hydrogen, by treatment with the appropriate metal alkoxide, for example, sodium methoxide.

Those 1-(Y)-2-(Y')-2-[3-(Z)-4-(Z')-phenyl]-1nitroethylenes of Formula XII which are not described in the chemical literature can be prepared, for example, by condensing under base catalysis the corresponding (Y)-nitromethane and the corresponding 3-(Z)-4-(Z')-benzaldehyde or 3-(Z)-4-(Z')-phenyl-(Y')-ketone of the formula

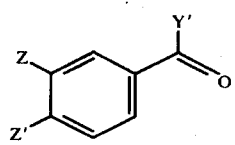
(Formula XIII).

Those 1-{1-(Y)-2-(Y')-2-[3-(Z)-4-(Z')-phenyl]ethyl}-3-(T$_n$-phenyl)ureas of Formula VII which are not described in the chemical literature are prepared by condensing the corresponding 1-(Y)-2-(Y')-2-[3-(Z)-4-(Z')-phenyl]ethylamines of Formula X with the corresponding T$_n$-phenylisocyanates of the formula

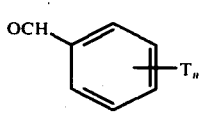
(Formula XIV).

Those T$_n$-phenylisocyanates which are not described in the chemical literature can be prepared, for example, by passing carbonyl chloride into hot solutions of the corresponding anilines in toluene, saturated with hydrogen chloride.

The following examples illustrate specific embodiments of my invention without limiting the latter thereto.

EXAMPLE 1

A solution of 3,4-dihydroisocarbostyril (IV: Y=Y'=Z=Z'=H) (64.3 g.) in dried methylene dichloride was added to a methylene dichloride (250 ml.) solution of triethyloxonium fluoborate, prepared from boron trifluoride etherate (227 g.), epichlorohydrin (74 g.) and absolute ether (600 ml.) After being stirred (for about 16 hr. at 25° C.), the mixture was treated with potassium carbonate solution (50%, 75 ml.) and water (25 ml.), stirred (for 1-½ hr.) and filtered. The solid material was washed thoroughly with methylene dichloride and dissolved in hot water. The solution was filtered and extracted three times with chloroform. 1-Ethoxy-3,4-dihydroisoquinoline fluoborate (10.5 g.) obtained in an earlier run was dissolved in potassium carbonate solution and the solution was extracted three times with methylene dichloride. The combined methylene dichloride washing, chloroform extract and methylene dichloride extract were stripped of solvents and distilled under reduced pressure, affording 1-ethoxy-3,4-dihydroisoquinoline (III: Q=$C_2H_5$, Y=Y'=Z=Z'=H) (68.4 g., b.p. 110°–137° C./16 mm. Hg), part (10.82 g.) of which was a center cut (b.p. 129°–131° C./16 mm. Hg). B. A solution of 1-ethoxy-3,4-dihydroisoquinoline (2.0 g.) in ethanol (10 ml.) was added dropwise with stirring to a solution (at 80° C.) of hydrazine (95%, 1.83 g.) in ethanol (5 ml.). The solution was concentrated, diluted with chloroform, washed with water, dried and concentrated. The residue (1.6 g.) was crystalized from ether in three crops (0.7 g., 0.5 g., 0.3 g.). Recrystallization of the first crop from ether-pentane afforded 1-hydrazino-3,4-dihydroisoquinoline (V: Y=Y'=Z=Z') (m.p. 55°–57° C.).

A mixture of 1-amino-3,4-dihydroisoquinoline (VI: R=R'=Y=Y'=Z=Z'=H) hydrochloride (m.p. 133°–134° C., 0.5 g.), prepared from 1-ethoxy-3,4-dihydroisoquinoline and ammonium chloride, sodium carbonate (0.38 g.), hydrazine (0.41 g.) and ethanol (15 ml.) was stirred (at 25° C.). The mixture was filtered. An ether solution of the crystals which separated from the filtrate on chilling was washed with water, dried and filtered. Concentration of the filtrate and crystallization of the residue from ether afforded 1-hydrazino-3,4-dihydroisoquinoline (0.44 g.).

Hydrazinolysis of 1-(p-methoxyanilino)-3,4-dihydroisoquinoline (VIII: T=$OCH_3$-p, n=1, Y=Y'=Z=Z'=H) (m.p. 105°–106.5° C.) afforded 1-hydrazino-3,4-dihydroisoquinoline.

A mixture of 1-ethoxy-3,4-dihydroisoquinoline (1.0 g.), hydrazine monohydrochloride (0.4 g.) and absolute ethanol (15 ml.) was heated under reflux (for 40 min.). The solution was cooled, filtered and concentrated and the residue was recrystallized from ethanol-ether, affording 1-hydrazino-3,4-dihydroisoquinoline hydrochloride (0.9 g., m.p. 205°–207° C.). C. A mixture of 1-hydrazino-3,4-dihydroisoquinoline (8.0 g.), acetaldehyde (20 ml.) and ethanol (20 ml.) was allowed to stand at room temperature (for 45 min). Ethanolic sulfuric acid was added until the solution was distinctly acidic. Ether was added. The resulting oil crystallized and the crystals were recrystallized from ethanol-ether, affording 1-(2-ethylidenehydrazino)-3,4-dihydroisoquinoline (I: X=$CH_3$, X'=Y=Y'=Z=Z'=H) sulfate in two crops (8.3 g., m.p. 152°–154° C.; 0.5 g., m.p. 152°–155° C.).

EXAMPLE 2

By substituting formaldehyde for acetaldehyde in Step C of Example 1, 1-(2-methylenehydrazine)-3,4-dihydroisoquinoline (I: X=X'X=Y=Y'=Z=Z'=H) sulfate is obtained.

EXAMPLE 3

By substituting isobutyraldehyde for acetaldehyde in Step C of Example 1, 1-(2-isobutylidenehydrazino)-3,4-dihydroisoquinoline (I: X=$(CH_3)_2CH$, X'=Y=Y'=Z=Z'=H) sulfate is obtained.

EXAMPLE 4

Valeraldehyde (5.14 g.) was added to a refluxing solution of 1-hydrazino-3,4-dihydroisoquinoline (8 g.) in ether (300 ml.). The mixture was allowed to stand (for 45 min.) at room temperature. Ethereal hydrochloric acid was added. Recrystallization of the resulting solid from ethanol-ether gave 1-(2-pentylidenehydrazino)-3,4-dihydroisoquinoline (I: X=$CH_3(CH_2)_3$, X'=Y=Y'=Z=Z'=H) hydrochloride in two crops (11.6 g. and 0.2 g., m.p. 147°–148° C.).

EXAMPLE 5

By substituting pivaldehyde for valeraldehyde in Example 4, 1-[2-(tert-butylmethylene)hydrazino]-3,4-dihydroisoquinoline (I: X=$(CH_3)_3C$, X'=Y=Y'=Z=Z'=H) hydrochloride is obtained.

EXAMPLE 6

In a manner similar to that of Example 4, condensation of 1-hydrazino-3,4-dihydroisoquinoline (11.0 g.) and tigladehyde (7.47 g.) and treatment of the product with sulfuric acid gave 1-[2-(2,3-dimethylallylidene)-hydrazino]-3,4-dihydroisoquinoline (I: X=$CH_3CH=C(CH_3)$, X'=Y=Y'=Z=Z'=H) sulfate (5.1 g., m.p. 231°–232° C. with decomposition).

EXAMPLE 7

By substituting cyclopentanecarboxaldehyde for valeraldehyde in Example 4, 1-[2-(cyclopentylmethylene)hydrazino]-3,4-dihydroisoquinoline (I: X=$CH_2(CH_2)_3CH$, X'=Y=Y'=Z=Z'=H) hydrochloride is obtained.

EXAMPLE 8

By substituting 3-cyclohexenecarboxaldehyde for valeraldehyde in Example 4, 1-[2-(3-cyclohexenylmethylene)hydrazino]-3,4-dihydroisoquinoline (I: X = $CH_2CH_2CH=CHCH_2CH$, X'=Y=Y'=Z=Z'=H) hydrochloride is obtained.

EXAMPLE 9

In a manner similar to that of Example 4, condensation of 1-hydrazino-3,4-dihydroisoquinoline (7 g.) and benzaldehyde (5.5 g.) and treatment of the reaction mixture with hydrochloric acid gave a solid, which was recrystallized from ethanol-ether, affording 1-(2-benzylidenehydrazino)-3,4-dihydroisoquinoline (I: X=$C_6H_5$, X'=Y=Y'=Z=Z'=H) hydrochloride (11.6 g., m.p. 226°–228° C.).

EXAMPLE 10

By substituting p-bromobenzaldehyde for valeraldehyde in Example 4, 1-[2-(p-bromobenzylidene)hydrazino]-3,4-dihydroisoquinoline (I: X=p-$BrC_6H_4$, X'=Y=Y'=Z=Z'=H) hydrochloride is obtained.

EXAMPLE 11

By substituting m-hydroxybenzaldehyde for valeraldehyde in Example 4, 1-[2-(m-hydroxybenzylidene)hydrazino]-3,4-dihydroisoquinoline (I: X=m-$HOC_6H_4$, X'=Y=Y'=Z=Z'=H) hydrochloride is obtained.

EXAMPLE 12

By substituting p-tolualdehyde for valeraldehyde in Example 4, 1-[2-(p-methylbenzylidene)hydrazino]-3,4-dihydroisoquinoline (I: X=p-$CH_3C_6H_4$, X'=Y=Y'=Z=Z'=H) hydrochloride is obtained.

EXAMPLE 13

In a manner similar to that of Example 4, condensation of 1-hydrazino-3,4-dihydroisoquinoline (5.7 g.) and 2,3-dimethoxybenzaldehyde (6.17 g.) and treatment of the reaction mixture with hydrochloric acid gave a solid, which was recrystallized twice from ethanol, affording 1-[2-(2,3-dimethoxybenzylidene)-hydrazino]-3,4-dihydroisoquinoline (I: X=2,3-(CH$_3$O)$_2$C$_6$H$_3$, X'=Y=Y'=Z=Z'=H) hydrochloride (8.2 g., m.p. 222°–223° C.).

EXAMPLE 14

In a manner similar to that of Example 4, condensation of 1-hydrazino-3,4-dihydroisoquinoline (10.0 g.) and syringaldehyde (12.5 g.) and treatment of the reaction mixture with hydrochloric acid gave a solid, which was recrystallized from N,N-dimethylformamide-ether, affording 1-[2-(3,5-dimethoxy-4-hydroxybenzylidene)-hydrazino]-3,4-dihydroisoquinoline (I: X=3,5-(CH$_3$O)$_2$-4-HOC$_6$H$_2$, X'=Y=Y'=Z=Z'=H) hydrochloride in two crops (total of 18 g., m.p. 232°–233° C.).

EXAMPLE 15

By substituting m-bromocinnamaldehyde for valeraldehyde in Example 4, 1-[2-(3-(m-bromo)phenylallylidene)-hydrazino]-3,4-dihydroisoquinoline (I: X = m-BrC$_6$H$_4$CH=CH, X' = Y = Y' = Z = Z' =H) hydrochloride is obtained.

EXAMPLE 16

By substituting p-hydroxycinnamaldehyde for valeraldehyde in Example 4, 1-[2-(3-(p-hydroxy)phenylallylidene)-hydrazino]-3,4-dihydroisoquinoline (I: X =p-HOC$_6$H$_4$CH=CH, X' = Y = Y' = Z = Z' = H) hydrochloride is obtained.

EXAMPLE 17

By substituting p-methylcinnamaldehyde for valeraldehyde in Example 4, 1-[2-(3-(p-methyl)phenylallylidene)-hydrazino]-3,4-dihydroisoquinoline (I: X = p-CH$_3$C$_6$H$_4$CH=CH, X' = Y = Y' =Z = Z' =H) hydrochloride is obtained.

EXAMPLE 18

A solution of 1-hydrazino-3,4-dihydroisoquinoline hydrochloride (9.88 g.) and p-methoxycinnamaldehyde (8.9 g.) in ethanol (200 ml.) was stirred at room temperature. A solid separated from the mixture, which was then chilled. The solid was washed with ether and recrystallized twice from ethanol, affording 1-[2-(3-(p-methoxy)phenylallylidene)hydrazino]-3,4-dihydroisoquinoline (I: X = p-CH$_3$OC$_6$H$_4$CH=CH, X' = Y = Y' = Z = Z' = H) hydrochloride (13 g., m.p. 225°–227° C.).

EXAMPLE 19

In a manner similar to that of Example 18 condensation of 1-hydrazino-3,4-dihydroisoquinoline hydrochloride (9.88 g.) and p-(dimethylamino)cinnamaldehyde (9.63 g.) and recrystallization of the resulting product (16 g.) from ethanol afforded 1-[2-(3-(p-dimethylamino)phenylallylidene)hydrazino]-3,4-dihydroisoquinoline (I: X = p-(CH$_3$)$_2$ NC$_6$H$_4$CH=CH,X' = Y = Y' = Z = Z' = H) hydrochloride (9.5 g., m.p. 227°–228° C.).

EXAMPLE 20

In a manner similar to that of Example 4, condensation of 1-hydrazino-3,4-dihydroisoquinoline (7.3 g.) and α-methylcinnamaldehyde (6.56 g.) and treatment of the reaction mixture with hydrochloric acid gave a solid, which was recrystallized first from ethanol-ether, then twice from N,N-dimethylformamide-ether, affording 1-[2-(2-methyl-3-phenylallylidene)hydrazino]-3,4-dihydroisoquinoline (I: X=C$_6$H$_5$CH=C(CH$_3$), X'=Y=Y'=Z=Z'=H) hydrochloride in two crops (5.6 g. and 4.2 g., m.p. 217°–219° C.).

EXAMPLE 21

In a manner similar to that of Example 18 condensation of 1-hydrazino-3,4-dihydroisoquinoline hydrochloride (9.88 g.) and α-methyl-p-fluorocinnamaldehyde (9.03 g., prepared by condensation of p-fluorobenzaldehyde and propionaldehyde) and two recrystallizations of the resulting product from isopropyl alcohol afforded 1-[2-(2-methyl-3-(p-fluoro)-phenylallylidene)hydrazino]-3,4-dihydroisoquinoline (I: X = p-FC$_6$H$_4$CH= C(CH$_3$), X' = Y = Y' = Z = Z' = H) hydrochloride (3.5 g., m.p. 198°–200° C.).

EXAMPLE 22

In a manner similar to that of Example 18 condensation of 1-hydrazino-3,4-dihydroisoquinoline hydrochloride (9.88 g.) and α-methyl-p-chlorocinnamaldehyde (9.9 g., prepared by condensation of p-chlorobenzaldehyde and propionaldehyde) and three recrystallizations of the resulting product from ethanol afforded 1-[2-(2-methyl-3-(p-chloro)phenylallyl-idene)hydrazino]-3,4-dihydroisoquinoline (I: X = p-ClC$_6$H$_4$CH= C(CH$_3$), X' = Y = Y' = Z = Z' = H) hydrochloride (mixture of cis and trans isomers, 8.5 g., m.p. 215°–217° C.).

EXAMPLE 23

In a manner similar to that of Example 18 condensation of 1-hydrazino-3,4-dihydroisoquinoline hydrochloride (9.88 g.) and α-methyl-o-chlorocinnamaldehyde (9.9 g., prepared by condensation of o-chlorobenzaldehyde and propionaldehyde) afforded 1-[2-(2-methyl-3-(o-chloro)phenylallylidene)-hydrazino]-3,4-dihydroisoquinoline (I: X = o-ClC$_6$H$_4$CH=C(CH$_3$), X' = Y = Y' = Z = Z' = H) hydrochloride (12 g., m.p. 243°–246° C.).

EXAMPLE 24

By substituting α,p-dimethylcinnamaldehyde for α-methylcinnamaldehyde in Example 20, 1-[2-(2-methyl-3-(p-methyl)phenylallylidene)hydrazino]-3,4-dihydroisoquinoline (I: X = p-CH$_3$C$_6$H$_4$CH= C(CH$_3$), X' = Y = Y' =Z = Z' = H) hydrochloride is obtained.

EXAMPLE 25

A solution of 1-hydrazino-3,4-dihydroisoquinoline (15.0 g.) and acetone (50 ml.) was warmed for several minutes on the steam bath, allowed to stand at room temperature (for 20 min.), then treated with cooling with a solution of concentrated sulfuric acid (6.6 ml.) in acetone. The resulting solid was triturated with acetone and recrystallized from methanolether, affording 1-(2-isopropylidenehydrazino)-3,4-dihydroisoquinolone (I: X=X'=CH$_3$, Y=Y'=Z=Z'=H) sulfate (24.0 g., m.p. 187°–189° C. with decomposition).

EXAMPLE 26

In a manner similar to that of Example 4, condensation of 1-hydrazino-3,4-dihydroisoquinoline (9.4 g.) and cyclohexanone (6.3 g.) and treatment of the reaction mixture with sulfuric acid gave an oil, which was crystallized, then recrystallized, from isopropyl alcohol-ether, affording 1-(2-cyclohexylidenehydrazino)-3,4-dihydroisoquinoline [(I:

$X=X'=CH_2(CH_2)_4C,$] $Y=Y'=Z=Z'=H$) sulfate (15.3 g., m.p. 139°–141° C. with decomposition).

EXAMPLE 27

A. To a suspension of amphetamine (X: $Y=CH_3$, $Y'=Z=Z'=H$) hydrochloride (100 g.) in ether was added a solution of triethylamine (130 g.) in ether (200 ml.) followed by a solution of ethyl chloroformate (70 g.) in ether. The mixture was stirred (for ¾ hr.), then filtered. The filtrate was stripped of ether and filtered, thus providing ethyl N-(3-phenyl-2-propyl)-carbamate (IX: $Y=CH_3$, $Y'=Z=Z'=H$) as a yellow oil (117.8 g.).

B. A mixture of ethyl N-(3-phenyl-2-propyl)carbamate (112 g.) and polyphosphoric acid (336 g.) was heated (at 155° C. for 1-½ hr.), cooled, diluted with ice, extracted three times with chloroform, neutralized with sodium hydroxide solution (35%) and extracted twice more with chloroform. The combined chloroform extracts were washed with water, dried, and stripped of solvent. Recrystallization of the resulting solid (31 g.) from ether afforded 3-methyl-3,4-dihydroisocarbostyril (IV: $Y=CH_3$, $Y'=Z=Z'=H$) (22.5 g.).

C. In a manner similar to that of Step A of Example 1, ethylation of 3-methyl-3,4-dihydroisocarbostyril (22.5 g.) with triethyloxonium fluoborate (0.3 mole) afforded 1-ethoxy-3-methyl-3,4-dihydroisoquinoline (III: $Q=C_2H_5$, $Y=CH_3$, $Y'=Z=Z'=H$) (20.7 g., b.p. 128°–129° C./15 mm. Hg).

D. In a manner similar to that of Step B of Example 1, condensation of 1-ethoxy-3-methyl-3,4-dihydroisoquinoline (1.0 g.) and hydrazine monohydrochloride (0.36 g.) and three recrystallizations of the resulting product from ethanol-ether afforded 1-hydrazino-3-methyl-3,4-dihydroisoquinoline (V: $Y=CH_3$, $Y'=Z=Z'=H$) hydrochloride (m.p. 174°–176° C.).

E. By substituting 1-hydrazino-3-methyl-3,4-dihydroisoquinoline for 1-hydrazino-3,4-dihydroisoquinoline in Example 25, 1-(2-isopropylidenehydrazino)-3-methyl-3,4-dihydroisoquinoline (I: $X=X'=Y=CH_3$, $Y'=Z=Z'=H$) sulfate is obtained.

EXAMPLE 28

By substituting 2-phenylpropylamine (X: $Y'=CH_3$, $Y=Z=Z'=H$) hydrochloride for amphetamine hydrochloride in Step A of Example 27 and carrying the resulting ethyl N-(2-phenylpropyl)carbamate (IX: $Y'=CH_3$, $Y=Z=Z'=H$) through Steps B-E, 1-(2-isopropylidenehydrazino)-4-methyl-3,4-dihydroisoquinoline (I: $X=X'=Y'=CH_3$, $Y=Z=Z'=H$) sulfate is obtained.

EXAMPLE 29

By substituting 3-phenyl-2-butylamine (X: $Y=Y'=CH_3$, $Z=Z'=H$) hydrochloride for amphetamine hydrochloride in Step A of Example 27 and carrying the resulting ethyl N-(2-phenyl-2-butyl)carbamate (IX: $Y=Y'=CH_3$, $Z=Z'=H$) through Steps B–E, 1-(2-isopropylidenehydrazino)-3,4-dimethyl-3,4-dihydroisoquinoline (I: $X=X'=Y=Y'=CH_3$, $Z=Z'=H$) sulfate is obtained.

EXAMPLE 30

By substituting 2,2-diphenylethylamine (X: $Y'=C_6H_5$, $Y=Z=Z'=H$) hydrochloride for amphetamine hydrochloride in Step A of Example 27 and carrying the resulting ethyl N-(2,2-diphenylethyl)carbamate (IX: $Y'=C_6H_5$, $Y=Z=Z'=H$) through Steps B–E, 1-(2-isopropylidenehydrazino)-4-phenyl-3,4-dihydroisoquinoline (I: $X=X'=CH_3$, $Y'=C_6H_5$, $Y=Z=Z'=H$) sulfate is obtained.

EXAMPLE 31

A. A solution of sodium hydroxide (134 g.) in water (250 ml.) was added to a suspension of 2-formylbenzoic acid (Xc: $Z=Z'=H$) (250 g.) in methanol-water (4:1, 1500 ml.) and the resulting mixture was stirred for 3-½ hr. at 0°–10° C. The solid obtained after acidification of the reaction mixture was recrystallized from ethanol, affording 1-(nitromethyl)-phthalide (Xb: $Y=Z=Z'=H$) in three crops (113 g., 14 g., 5.2 g.).

B. A mixture of 1-(nitromethyl)phthalide (26.5 g.), concentrated hydrochloric acid (11.5 ml.), palladium-on-carbon (3 g.) and ethanol (to make a total of 600 ml.) was hydrogenated under pressure (45 p.s.i.g.). The solution was concentrated under reduced pressure in the presence of benzene, affording 1-(aminomethyl)phthalide (Xa: $Y=Z=Z'=H$) hydrochloride (10.5 g.).

C. A mixture of 1-(aminomethyl)phthalide (5g.) and sodium hydroxide solution (0.988 N, 51 ml.) was refluxed for 6 hr. under nitrogen, filtered, concentrated and salted. The solids obtained by filtering the resulting mixture and evaporating the filtrate to dryness were triturated with ethyl acetate, affording 4-hydroxy-3,4-dihydroisocarbostyril (IV: $Y'=OH$, $Y=Z=Z'=H$) in two crops (2.1 g., 0.4 g.).

D. In a manner similar to that of Step A of Example 1, ethylation of 4-hydroxy-3,4-dihydroisocarbostyril (21.75 g.) with triethyloxonium fluoborate (0.147 + 0.073/3 mole) and two recrystallizations (the first recrystallization afforded a first crop of 8 g., of which 4.2 g. was recrystallized) of the resulting product from ethanol-ether afforded 1-ethoxy-4-hydroxy-3,4-dihydroisoquinoline (III: $Q=C_2H_5$, $Y'=OH$, $Y=Z=Z'=H$) fluoborate (3.9 g., m.p. 121°–123° C.).

E. A solution of hydrazine (95%, 1.46 g.) in ethanol (150 ml.) was added to a solution of 1-ethoxy-4-hydroxy-3,4-dihydroisoquinoline fluoborate (12.0 g.) in ethanol (120 ml.). After about 5 hr. the resulting mixture was filtered and the filtrate was evaporated to dryness. Two recrystallizations of the residue from ethanol-ether and then one recrystallization from isopropyl alcohol afforded 1-hydrazino-4-hydroxy-3,4-dihydroisoquinoline (V: $Y'=OH$, $Y=Z=Z'=H$) fluoborate (7.38 g., m.p. 147°–148° C.).

F. By substituting 1-hydrazino-4-hydroxy-3,4-dihydroisoquinoline for 1-hydrazino-3,4-dihydroisoquinoline in Example 25, 1-(2-isopropylidenehydrazino)-4-hydroxy-3,4-dihydroisoquinoline (I: $X=X'=CH_3$, $Y'=OH$, $Y$ 32 $Z=Z'=H$) sulfate is obtained.

EXAMPLE 32

By substituting 2-methoxy-2-phenylethylamine (X: $Y'=CH_3O$, $Y=Z=Z'=H$) hydrochloride for amphetamine hydrochloride in Step A of Example 27 and carrying the resulting ethyl N-(2-methoxy-2-phenylethyl)carbamate (IX: $Y'=CH_3O$, $Y=Z=Z'=H$) through Steps B–E, 1-(2-isopropylidenedhydrazino)-4-methoxy-3,4-dihydroisoquinoline (I: $X=X'=CH_3$, $Y'=CH_3O$, $Y=Z=Z'=H$) sulfate is obtained.

EXAMPLE 33

By substituting 2-(p-tolyl)ethylamine (X: $Z'=CH_3$, $Y=Y'=Z=H$) hydrochloride for amphetamine hydrochloride in Step A of Example 27 and carrying the resulting ethyl N-[2-(p-tolyl)-ethyl]carbamate (IX: Z'=C₃, Y=Y'=Z=H) through Steps B–E, 1-(2-isopropylidenehydrazino)-7-methyl-3,4-dihydroisoquinoline (I: X=X'=Z'CH₃, Y=Y'=Z=H) sulfate is obtained.

EXAMPLE 34

By substituting 2-(m-chlorophenyl)ethylamine (X: Z=Cl, Y=Y'=Z'=H) hydrochloride for amphetamine hydrochloride in Step A of Example 27 and carrying the resulting ethyl N-[2-(m-chlorophenyl)ethyl]carbamate (IX: Z=Cl, Y=Y'=Z'=H) through Steps B–E, 1-(2-isopropylidenehydrazino)-6-chloro-3,4-dihydroisoquinoline (I: X=X'=CH₃, Z=Cl, Y=Y'=Z'=H) sulfate is obtained.

EXAMPLE 35

By substituting 2-(m-hydroxyphenyl)ethylamine (X: Z=HO, Y=Y'=Z'=H) hydrochloride for amphetamine hydrochloride in Step A of Example 27 and carrying the resulting ethyl N-[2-(m-hydroxyphenyl)ethyl]carbamate (IX: Z=OH, Y=Y'=Z'=H) through Steps B–E, 1-(2-isopropylidenedhydrazino)-6-hydroxy-3,4-dihydroisoquinoline (I: X=X'=CH₃, Z=HO, Y=Y'=Z'=H) sulfate is obtained.

EXAMPLE 36

By substituting 2-(m-methoxyphenyl)ethylamine (X: Z=CH₃O, Y=Y'=Z'H) hydrochloride for amphetamine hydrochloride in Step A of Example 27 and carrying the resulting ethyl N-[2-(m-methoxyphenyl)ethyl]carbamate (IX: Z=CH₃O, Y=Y'=Z'=H) through Steps B–E, 1-(2-isopropylidenehydrazino)-6-methoxy-3,4-dihydroisoquinoline (I: X=X'=CH₃, Z=CH₃O, Y=Y'=λ Z'=H) sulfate is obtained.

EXAMPLE 37

A. In a manner similar to that of Step A of Example 27, condensation of homoveratrylamine (X: Y=Y'=H, Z=Z'=CH₃O) (100 g.) and methyl chloroformate (52.2 g.) afforded methyl N-[2-(3,4-dimethoxyphenyl)ethyl]carbamate (IX: Y=Y'=H, Z=Z'=CH₃O) (90.0 g., b.p. 143°–163° C./0.05–0.06 mm. Hg).

B. In a manner similar to that of Step B of Example 27, cyclization of N-[2-(3,4-dimethoxyphenyl)ethyl]carbamate (89.0 g.) afforded 6,7-dimethoxy-3,4-dihydroisocarbostyril (IV: Y=Y' =H, Z=Z'=CH₃O) (19.6 g.) after recrystallization from toluene.

C. In a manner similar to that of Step A of Example 1, ethylation of 6,7-dimethoxy-3,4-dihydroisocarbostyril (14.0 g.) afforded 1-ethoxy-6,7-dimethoxy-3,4-dihydroisoquinoline (III: Q=C₂H₅, Y=Y'=H, Z=Z'=CH₃O) (12.6 g.) after recrystallization from ethyl acetate.

D. In a manner similar to that of Step B of Example 1, hydrazinolysis of 1-ethoxy-6,7-dimethoxy-3,4-dihydroisoquinoline (15.85 g.) afforded 1-hydrazino-6,7-dimethoxy-3,4-dihydroisoquinoline (V: Y=Y'=H, Z=Z'=CH₃O) (9.5 g.)

E. In a manner similar to that of Step C of Example 1, condensation of 1-hydrazino-6,7-dimethoxy-3,4-dihydroisoquinoline (7.2 g.) with acetaldehyde (4.3 g.) and treatment of the resulting product with sulfuric acid afforded 1-(2-ethylidenehydrazino)-6,7-dimethoxy-3,4-dihydroisoquinoline (I: X=CH₃, X'=Y=Y'=H, Z=Z'=CH₃O) sulfate monohydrate (5.3 g., m.p. 165°–168° C.).

EXAMPLE 38

In a manner similar to that of Example 25, condensation of 1-hydrazino-6,7-dimethoxy-3,4-dihydroisoquinoline (7.0 g.) and acetone (100 ml.) and treatment of the reaction mixture with hydrochloric acid afforded 1-(2-isopropylidenehydrazino)-6,7-dimethoxy-3,4-dihydroisoquinoline (I: X = X' = CH₃, Y = Y' = H, Z = Z' = CH₃O) hydrochloride (7.55 g., m.p. 211.5°–213° C. with decomposition).

EXAMPLE 39

In a manner similar to that of Example 18 condensation of 1-hydrazino-6,7-dimethoxy-3,4-dihydroisoquinoline hydrochloride (9 g.) and α-methylcinnamaldehyde (5.62 g.) and recrystallization of the resulting product first from ethanol-methanol and then from ethanol-water afforded 1-[2-(2-methyl-3-phenylallylidene)hydrazino]-6,7-dimethoxy-3,4-dihydroisoquinoline (I: X= C₆H₅CH=C(CH₃), X' = Y = Y' = H, Z = Z' = CH₃O) hydrochloride monohydrate (10.2 g., m.p. 215°–217° C.).

EXAMPLE 40

By substituting 2(3,4-methylenedioxyphenyl)ethylamine (X: Y=Y'=H, Z+Z'=OCH₂O) hydrochloride for amphetamine hydrochloride in Step A of Example 27 and carrying the resulting ethyl N-[2-(3,4-methylenedioxyphenyl)ethyl]carbamate (IX: Y=Y'=H, Z+Z'λ =OCH₂O) through Steps B–E, 1-(2-isopropylidenehydrazino)-6,7-methylenedioxy-3,4-dihydroisoquinoline (I: X=X'=CH₃, Y=Y'H, Z+Z'=OCH₂O) sulfate is obtained.

EXAMPLE 41

A. A solution of 1-ethoxy-3,4-dihydroisoquinoline (4.25 g.) and 1-hydrazino-3,4-dihydroisoquinoline (3.9 g.) in methanol (40 ml.) was stirred at room temperature overnight and then at reflux for a day. More 1-ethoxy-3,4-dihydroisoquinoline (1 g.) was added during the reflux period. The solution was stripped of methanol and the solid was recrystallized from 2-propanol, affording 1,1'-azinobis(1,2,3,4-tetrahydroisoquinoline) (II: Y=Y'=Z=Z'H) (first crop, 2.6 g., m.p. 178°–179° C.). In this example 1-hydrazino-3,4-dihydroisoquinoline hydrochloride can be used instead of 1-hydrazino-3,4-dihydroisoquinoline.

B. 1,1'-Azinobis(1,2,3,4-tetrahydroisoquinoline) was also obtained by a combination of fractional crystallization and elution chromatography of the residues from the mother liquors of crystallization of 1-hydrazino-3,4-dihydroisoquinoline obtained from a hydrazinolysis of 1-ethoxy-3,4-dihydroisoquinoline (72 g.) by the method of Step B of Example 1. The material so obtained was combined with the second crop (0.4 g.) of material from the recrystallization in Part A of this Example and recrystallized from 2-propanol (1.4 g., m.p. 178°–179° C.).

EXAMPLE 42

The reaction between 1-ethoxy-3-methyl-3,4-dihydroisoquinoline and hydrazine, which produced 1-hydrazino-3-methyl-3,4-dihydroisoquinoline, also produced a dimer, recrystallization of which from methanol-ethanol afforded 1,1'-azinobis(3-methyl-1,2,3,4-tetrahydroisoquinoline) (II: Y=CH₃, Y'=Z=Z'=H) (2.2 g., m.p. 168°–171° C.).

EXAMPLE 43

By substituting 1-ethoxy-4-methyl-3,4-dihydroisoquinoline from Step C of Example 28 for 1-ethoxy-3,4-dihydroisoquinoline and 1-hydrazino-4-methyl-3,4-dihydroisoquinoline from Step D of Example 28 for 1-hydrazino-3,4-dihydroisoquinoline in Part A of Example 41, 1,1'-azinobis(4-methyl-1,2,3,4-tetrahydroisoquinoline) (II: Y'=$CH_3$, Y=Z=Z'=H) is obtained.

EXAMPLE 44

By substituting 1-ethoxy-3,4-dimethyl-3,4-dihydroisoquinoline from Step C of Example 29 for 1-ethoxy-3,4-dihydroisoquinoline and 1-hydrazino-3,4-dimethyl-3,4-dihydroisoquinoline from Step D of Example 29 for 1-hydrazino-3,4-dihydroisoquinoline in Part A of Example 41, 1,1'-azinobis(3,4-dimethyl-1,2,3,4-tetrahydroisoquinoline) (II: Y=Y'=$CH_3$, Z=Z'=H) is obtained.

EXAMPLE 45

By substituting 1-ethoxy-4-phenyl-3,4-dihydroisoquinoline from Step C of Example 30 for 1-ethoxy-3,4-dihydroisoquinoline and 1-hydrazino-4-phenyl-3,4-dihydroisoquinoline from Step D of Example 30 for 1-hydrazino-3,4-dihydroisoquinoline in Part A of Example 41, 1,1'-azinobis(4-phenyl-1,2,3,4-tetrahydroisoquinoline) (II: Y'=$C_6H_5$, Y=Z=Z'=H) is obtained.

EXAMPLE 46

By substituting 1-ethoxy-4-hydroxy-3,4-dihyroisoquinoline from Step C of Example 31 for 1-ethoxy-3,4-dihydroisoquinoline and 1-hydrazino-4-hydroxy-3,4-dihydroisoquinoline from Step D of Example 31 for 1-hydrazino-3,4-dihydroisoquinoline in Part A of Example 41, 1,1'-azinobis(4-hydroxy-1,2,3,4-tetrahydroisoquinoline) (II: Y'=HO, Y=Z=Z'=H) is obtained.

EXAMPLE 47

By substituting 1-ethoxy-4-methoxy-3,4-dihydroisoquinoline from Step C of Example 32 for 1-ethoxy-3,4-dihydroisoquinoline and 1-hydrazino-4-methoxy-3,4-dihydroisoquinoline from Step D of Example 32 for 1-hydrazino-3,4-dihydroisoquinoline in Part A of Example 41, 1,1'-azinobis(4-methoxy-1,2,3,4-tetrahydroisoquinoline) (II: Y'=$CH_3O$, Y=Z=Z'=H) is obtained.

EXAMPLE 48

By substituting 1-ethoxy-7-methyl-3,4-dihydroisoquinoline from Step C of Example 33 for 1-ethoxy-3,4-dihydroisoquinoline and 1-hydrazino-7-methyl-3,4-dihydroisoquinoline from Step D of Example 33 for 1-hydrazino-3,4-dihydroisoquinoline in Part A of Example 41, 1,1'-azinobis(7-methyl-1,2,3,4-tetrahydroisoquinoline) (II: Y=Y'=Z=H, Z'=$CH_3$) is obtained.

EXAMPLE 49

By substituting 1-ethoxy-6-chloro-3,4-dihydroisoquinoline from Step C of Example 34 for 1-ethoxy-3,4-dihydroisoquinoline and 1-hydrazino-6-chloro-3,4-dihydroisoquinoline from Step D of Example 34 for 1-hydrazino-3,4-dihydroisoquinoline in Part A of Example 41, 1,1'-azinobis(6-chloro-1,2,3,4-tetrahydroisoquinoline) (II: Y=Y'=Z'=H, Z=Cl) is obtained.

EXAMPLE 50

By substituting 1-ethoxy-6-hydroxy-3,4-dihydroisoquinoline from Step C of Example 35 for 1-ethoxy-3,4-dihydroisoquinoline and 1-hydrazino-6-hydroxy-3,4-dihydroisoquinoline from Step D of Example 35 for 1-hydrazino-3,4-dihydroisoquinoline in Part A of Example 41, 1,1'-azinobis(6-hydroxy-1,2,3,4-tetrahydroisoquinoline) (II: Y=Y'=Z'=H, Z=HO) is obtained.

EXAMPLE 51

By substituting 1-ethoxy-6-methoxy-3,4-dihydroisoquinoline from Step C of Example 36 for 1-ethoxy-3,4-dihydroisoquinoline and 1-hydrazino-6-methoxy-3,4-dihydroisoquinoline from Step D of Example 36 for 1-hydrazino-3,4-dihydroisoquinoline in Part A of Example 41, 1,1'-azinobis(6-methoxy-1,2,3,4-tetrahydroisoquinoline) (II: Y=Y'=Z'=H, Z=$CH_3O$) is obtained.

EXAMPLE 52

By substituting 1-ethoxy-6,7-dimethoxy-3,4-dihydroisoquinoline from Step C of Example 37 for 1-ethoxy-3,4-dihydroisoquinoline and 1-hydrazino-6,7-dimethoxy-3,4-dihydroisoquinoline from Step D of Example 37 for 1-hydrazino-3,4-dihydroisoquinoline in Part A of Example 41, 1,1'-azinobis(6,7-dimethoxy-1,2,3,4-tetrahydroisoquinoline) (II: Y=Y'=H, Z=Z'=$CH_3O$) is obtained.

EXAMPLE 53

By substituting 1-ethoxy-6,7-methylenedioxy-3,4-dihydroisoquinoline from Step C of Example 40 for 1-ethoxy-3,4-dihydroisoquinoline and 1-hydrazino-6,7-methylenedioxy-3,4-dihydroisoquinoline from Step D of Example 40 for 1-hydrazino-3,4-dihydroisoquinoline in Part A of Example 41, 1,1'-azinobis(6,7-methylenedioxy-1,2,3,4-tetrahydroisoquinoline) (II: Y=Y'=H, Z+Z'=$OCH_2O$) is obtained.

I claim:

1. 1-(QO)-3-(Y)-4-(Y')-6-(Z)-7-(Z')-3,4-dihydroisoquinoline of the formula

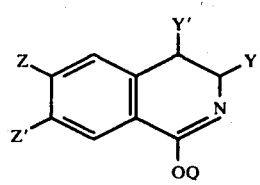

wherein Q is methyl, ethyl or propyl;

Y is hydrogen or a tertiary alkyl of one to four carbon atoms;

Y' is hydrogen, a tertiary alkyl of one to four carbon atoms, phenyl, hydroxy or a tertiary alkoxy of one to four carbon atoms;

Z and Z', when taken alone, are the same or different and are hydrogen, a tertiary alkyl of one to four carbon atoms, halo, hydroxy or a tertiary alkoxy of one to four carbon atoms;

Z and Z', when taken together, are methylenedioxy; and acid addition salts thereof.

2. 1-(QO)-3-(Y)-4-(Y')-6-(Z)-7-(Z')-3,4-dihydroisoquinoline wherein Y and Y' are each hydrogen according to claim 1.

3. 1-Ethoxy-3,4-dihydroisoquinoline according to claim 2.

4. 1-(QO)-3-(Y)-4-(Y')-6-(Z)-7-(Z')-3,4-dihydroisoquinoline wherein Z and Z' are each a tertiary alkoxy of one to four carbon atoms according to claim 2.

5. 1-Ethoxy-6,7-dimethoxy-3,4-dihydroisoquinoline according to claim 4.

* * * * *